(12) United States Patent
Mathan et al.

(10) Patent No.: US 7,991,195 B2
(45) Date of Patent: Aug. 2, 2011

(54) TARGET SPECIFIC IMAGE SCALING FOR EFFECTIVE RAPID SERIAL VISUAL PRESENTATION

(75) Inventors: Santosh Mathan, Minneapolis, MN (US); Patricia M. Ververs, Ellicott City, MD (US); Stephen D. Whitlow, Saint Louis Park, MN (US); Michael C. Dorneich, St. Paul, MN (US)

(73) Assignee: Honeywell International Inc., Morristown, NJ (US)

( * ) Notice: Subject to any disclaimer, the term of this patent is extended or adjusted under 35 U.S.C. 154(b) by 603 days.

(21) Appl. No.: 12/036,763

(22) Filed: Feb. 25, 2008

(65) Prior Publication Data

US 2009/0214118 A1 Aug. 27, 2009

(51) Int. Cl.
*G06K 9/00* (2006.01)
(52) U.S. Cl. ................... 382/103; 382/107; 382/254
(58) Field of Classification Search .............. 382/107, 382/103, 254
See application file for complete search history.

(56) References Cited

U.S. PATENT DOCUMENTS

| | | | |
|---|---|---|---|
| 5,239,591 A | 8/1993 | Ranganath | |
| 5,734,739 A | 3/1998 | Sheehan et al. | |
| 5,850,490 A | 12/1998 | Johnson | |
| 5,887,082 A | 3/1999 | Mitsunaga et al. | |
| 6,195,458 B1 | 2/2001 | Warnick et al. | |
| 6,417,841 B1 | 7/2002 | Doi et al. | |
| 6,418,430 B1 | 7/2002 | DeFazio et al. | |
| 6,421,463 B1 | 7/2002 | Poggio et al. | |
| 6,694,047 B1 | 2/2004 | Farrokhnia et al. | |
| 6,847,379 B2 | 1/2005 | Grosvenor et al. | |
| 6,898,316 B2 | 5/2005 | Zhou | |
| 7,039,256 B2 | 5/2006 | Zlotnick et al. | |
| 7,194,114 B2 | 3/2007 | Schneiderman | |
| 7,239,737 B2 | 7/2007 | Luque et al. | |
| 2005/0084136 A1 | 4/2005 | Xie et al. | |
| 2005/0196030 A1* | 9/2005 | Schofield et al. | 382/132 |
| 2005/0226463 A1* | 10/2005 | Suzuki et al. | 382/103 |

OTHER PUBLICATIONS

Sajda, P.; Gerson, A.; Parra, L.; , "High-throughput image search via single-trial event detection in a rapid serial visual presentation task," Neural Engineering, 2003. Conference Proceedings. First International IEEE EMBS Conference on , vol., No., pp. 7-10, Mar. 20-22, 2003.*
Gerson, A., et al., Cortical Origins of Response Time Variability During Rapid Discrimination of Visual Objects, NeuroImage, May 23, 2005.
Issen, Laurel, Using edge statistics for object recognition, May 15, 2006.
Peters, R., et al., Image Complexity Metrics for Automatic Target Recogniziers, 1990 Automatic Target Recognizers System and Technology Conference, Oct. 30-31, 1990.

* cited by examiner

*Primary Examiner* — Hadi Akhavannik
(74) *Attorney, Agent, or Firm* — Ingrassia Fisher & Lorenz, P.C.

(57) ABSTRACT

A system and method of efficiently and effectively triaging an image that may include one or more target entities are provided. A target entity to be searched for in the image is specified. The image, or at least a selected portion of the image, is then divided into a plurality of individual image chips each having a chip size based on the specified target entity. Each image chip is then successively displayed for a presentation time period.

17 Claims, 4 Drawing Sheets

TARGET SPECIFIC IMAGE SCALING FOR EFFECTIVE RAPID SERIAL VISUAL PRESENTATION

STATEMENT REGARDING FEDERALLY SPONSORED RESEARCH OR DEVELOPMENT

This invention was made with Government support under contract HM1582-05-C-0046 awarded by the Defense Advanced Research Projects Agency (DARPA). The Government has certain rights in this invention.

TECHNICAL FIELD

The present invention generally relates to a system and method for efficiently conducting image triage and, more particularly, to a system and method for efficiently conducting target specific high speed image triage.

BACKGROUND

Analysts in various professions may, at times, be called upon to search relatively large collections of imagery to identify, if present, various types of relevant information (referred to herein as "a target entity" or "target entities") in the collection of imagery. For example, medical analysts sometimes diagnose a physical impairment by searching complex imagery collections to identify one or more target entities therein that may be the cause of the physical impairment. Moreover, intelligence analysts may be called upon to search relatively complex imagery collections to identify target entities therein that may relate to various types of intelligence gathering activities.

Advancements in both image collection and storage technology presently allow for the relatively low-cost storage of large volumes of high-quality imagery. However, the cost of searching through large sets of imagery for target entities can often be substantial. Indeed, in many professions, such as intelligence gathering, effective searching may rely on the expertise of highly skilled analysts, who typically search through relatively large sequences of images in a relatively slow manner. Presently, the number of skilled analysts available to search the amount of imagery that is stored, or can potentially be stored, is in many instances insufficient.

In response to the foregoing, there has relatively recently been a focus on developing various systems and methods for triaging imagery. One of the methods that has shown promise combines electroencephalography (EEG) technology and rapid serial visualization presentation (RSVP). Various implementations of this combination have been researched and developed. For example, various researchers have experimented with a system in which users are presented, using the RSVP paradigm, a sequence of images, some of which may include particular types of target entities. During the RSVP presentation, EEG data are collected from the users. A classifier then uses the collected EEG data to assign probabilities to each image. The probabilities are representative of the likelihood an image includes a target.

Although useful in sorting a sequence of images, the above described system and method, as well as other systems and methods that employ these same technologies, do suffer certain drawbacks. For example, the effectiveness of this approach may depend on the appropriate dimensions of each image that is presented to the user. If the dimensions of the presented images are too large relative to a target entity, such target entities may be difficult to detect at relatively fast presentation rates. Alternatively, if the dimensions of the presented images are too small relative to a target entity, the overall search can be inefficient and relatively important details used to recognize the target entity may be lost.

Hence, there is a need for an efficient and effective system and method for increasing the likelihood of target entity identification in images. The present invention addresses at least this need.

BRIEF SUMMARY

In one embodiment, and by way of example only, a method of conducting image triage of an image that may include one or more target entities includes specifying a target entity to be searched for in the image. The image is divided into a plurality of individual image chips. Each image chip has a chip size based on the specified target entity. Each image chip is successively displayed for a presentation time period.

In yet another exemplary embodiment, a system for conducting image triage of an image that may include one or more target entities includes a display device, a user interface, and a processor. The display device is operable to receive display commands and, in response thereto, to display an image. The user interface is configured to receive input from a user and is operable, in response to the input from the user, to at least supply user interface signals representative of a target entity to be searched for. The processor is coupled to the display device and the user interface. The processor is configured to selectively retrieve an image, divide the image into a plurality of individual image chips each having a chip size based on the target entity to be searched for, and successively command the display device to display each image chip for a presentation time period.

Furthermore, other desirable features and characteristics of the image triage system and method will become apparent from the subsequent detailed description and the appended claims, taken in conjunction with the accompanying drawings and this background.

BRIEF DESCRIPTION OF THE DRAWINGS

The present invention will hereinafter be described in conjunction with the following drawing figures, wherein like numerals denote like elements, and wherein.

DETAILED DESCRIPTION OF A PREFERRED EMBODIMENT

The following detailed description of the invention is merely exemplary in nature and is not intended to limit the invention or the application and uses of the invention. Furthermore, there is no intention to be bound by any theory presented in the preceding background or the following detailed description.

Figure 1:
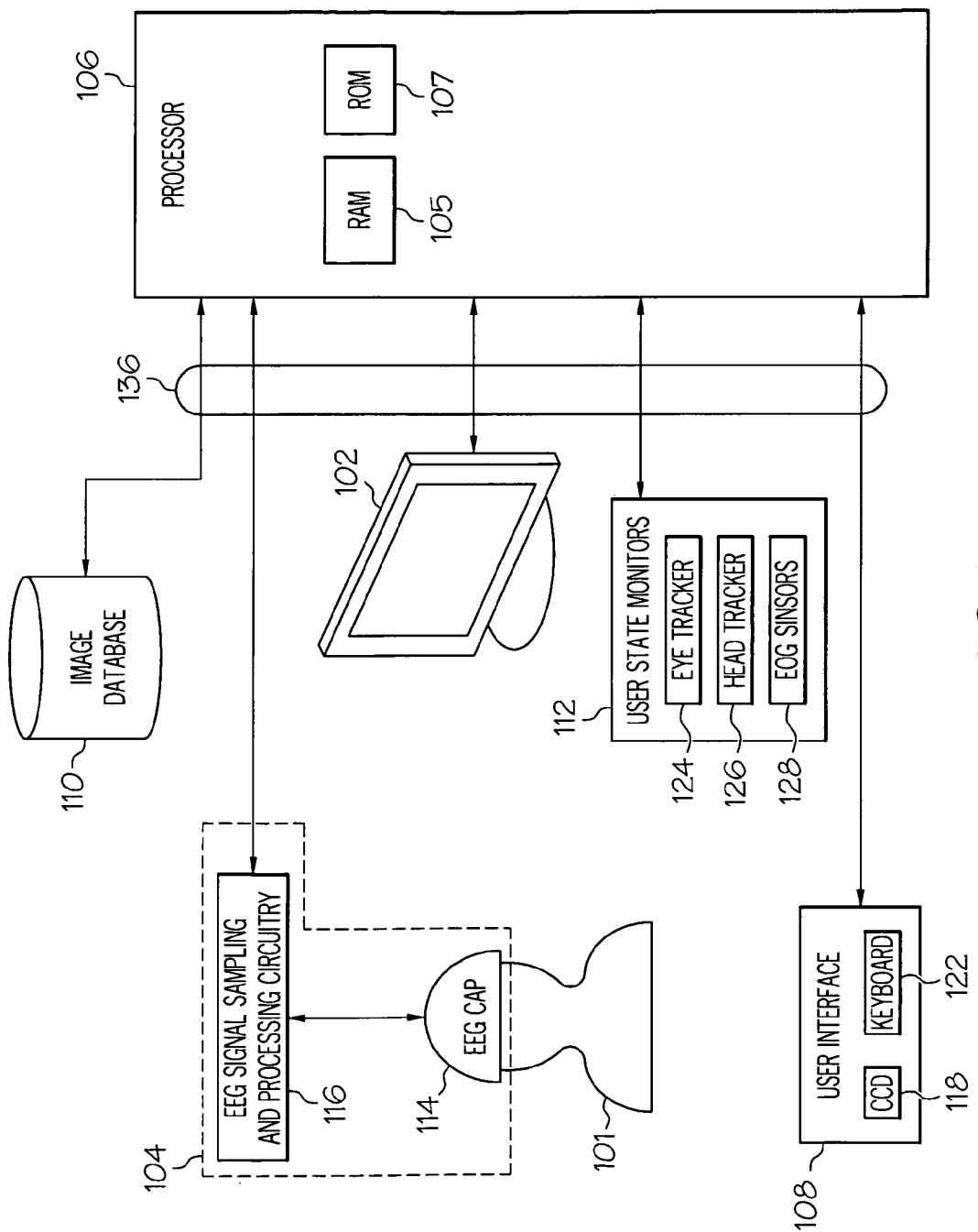
FIG. 1 depicts a functional block diagram of an exemplary image triaging system.

Turning first to FIG. 1, a functional block diagram of an exemplary system 100 that may be used to triage images is depicted. The depicted system 100 includes a display device 102, a data collector 104, and a processor 106. As FIG. 1 further depicts, in some embodiments the system 100 may additionally include a user interface 108, an image database 110, and one or more user state monitors 112. The display device 102 is in operable communication with the processor 106 and, in response to display commands received therefrom, displays one or more images to a user 101. It will be appreciated that the display device 102 may be any one of numerous known displays suitable for rendering graphic, icon, and/or textual images in a format viewable by the user 101. Non-limiting examples of such displays include various cathode ray tube (CRT) displays, and various flat panel displays such as, for example, various types of LCD (liquid crystal display) and TFT (thin film transistor) displays. The display may additionally be based on a panel mounted display, a head up display (HUD) projection, or any known technology.

The data collector 104 in the depicted embodiment is a neurophysiological data collector that is configured to be disposed on, or otherwise coupled to, the user 101, and is operable to selectively collect neurophysiological data from the user 101. Preferably, and as depicted in FIG. 1, the neurological data collector 104 is implemented as an electroencephalogram (EEG) system, and most preferably as a multi-channel EEG cap 114, and appropriate EEG signal sampling and processing circuitry 116. It will be appreciated that the number of EEG channels may vary. Moreover, the EEG signal sampling and processing circuitry 116 may be implemented using any one of numerous known suitable circuits and devices including, for example, one or more analog-to-digital converters (ADC), one or more amplifiers, and one or more filters. No matter the particular number of EEG channels and the particular type of EEG signal sampling and processing circuitry 116 that is used, it is in operable communication with, and is configured to supply the collected EEG data to, the processor 106. As will be described in more detail further below, the EEG signal sampling and processing circuitry 116 is further configured to receive trigger signals from the processor 106, and to record the receipt of these trigger signals concurrently with the EEG signals.

The user interface 108 is in operable communication with the processor 106 and is configured to receive input from the user 101 and, in response to the user input, supply various user interface signals to the processor 106. The user interface 108 may be any one, or combination, of various known user interface devices including, but not limited to, a cursor control device (CCD), such as a mouse, a trackball, or joystick, and/or a keyboard, one or more buttons, switches, or knobs. In the depicted embodiment, the user interface 102 includes a CCD 118 and a keyboard 122. The user 101 may use the CCD 118 to, among other things, move a cursor symbol on the display device 102 and select regions of an image displayed on the display device 102, and may use the keyboard 122 to, among other things, input various data. As will be described further below, the user 101 may additionally use either the CCD 118 or keyboard 122 to selectively supply physical response data, the purpose of which are also described further below.

The one or more user state monitors 112, if included, are operable to selectively collect various data associated with the user 101. The one or more user state monitors 112 may include at least an eye tracker 124, a head tracker 126, and one or more EOG (electrooculogram) sensors 128. The eye tracker 124, if included, is configured to detect the movement of one or both of the user's pupils. The head tracker 126, if included, is configured to detect the movement and/or orientation of the user's head. The EOG sensors 128, if included, are used to detect eye blinks and various eye movements of the user 101. Although any one of numerous devices may be used to implement the eye tracker 124 and head tracker 126, in the depicted embodiment one or more appropriately mounted and located video devices, in conjunction with appropriate processing software components are used to implement these functions. Though not explicitly depicted in FIG. 1, appropriate signal sampling and processing circuitry, if needed or desired, may be coupled between the eye tracker 124 and/or the head tracker 126 and the processor 106. Moreover, the same or similar signal sampling and processing circuitry 116 that is used with the EEG cap 114 may additionally be used to supply appropriate EOG signals to the processor 106. It will be appreciated that, at least in some embodiments, the system 100 may be implemented without one or all of the user state monitors 112. No matter which, if any, of the user state monitors 112 that are included in the system 100, each supplies appropriate user state data to the processor 106.

The processor 106 is in operable communication with the display device 102, the neurophysiological data collector 104, the user interface 108, and the image database 110 via, for example, one or more communication buses or cables 136. The processor 106 is coupled to receive neurophysiological data from the neurophysiological data collector 104. As noted above, the processor 106 may additionally receive physical response data from the user interface 108. As will be described in more detail further below, the processor 106, based at least in part on one or more of these data, assigns probabilities to discrete sections of an image. The assigned probabilities are representative of the likelihood that the discrete sections of the image include a target entity.

It was additionally noted above that the processor 106, at least in some embodiments, may also receive user state data from the one or more user state monitors 112. In such embodiments, the processor 106 appropriately processes the user data and the neurophysiological data to determine whether one or more of these data, either alone or in combination, indicate the user 101 is in a state that could adversely compromise the effectiveness of the image triage processing, which is described in more detail further below. It is noted that, based on this determination, the processor 106 may generate one or more user alerts and/or vary the pace of one or more portions of the below-described image triage processing.

The processor 106 may include one or more microprocessors, each of which may be any one of numerous known general-purpose microprocessors or application specific processors that operate in response to program instructions. In the depicted embodiment, the processor 106 includes on-board RAM (random access memory) 105, and on-board ROM (read only memory) 107. The program instructions that control the processor 106 may be stored in either or both the RAM 105 and the ROM 107. For example, the operating system software may be stored in the ROM 107, whereas various operating mode software routines and various operational parameters may be stored in the RAM 105. It will be appreciated that this is merely exemplary of one scheme for storing operating system software and software routines, and that various other storage schemes may be implemented. It will also be appreciated that the processor 106 may be implemented using various other circuits, not just one or more programmable processors. For example, digital logic circuits and analog signal processing circuits could also be used.

The image database 110 preferably has various types of imagery collections stored therein. The imagery collection types may vary, and may include, for example, various types of static imagery and various types of video imagery. It will additionally be appreciated that, although the image database 110 is, for clarity and convenience, shown as being stored separate from the processor 106, all or portions of this database 110 could be loaded into the on-board RAM 105, or integrally formed as part of the processor 106, and/or RAM 105, and/or ROM 107. The image database 110, or the image data forming portions thereof, could also be part of one or more non-illustrated devices or systems that are physically separate from the depicted system 100.

Figure 2:
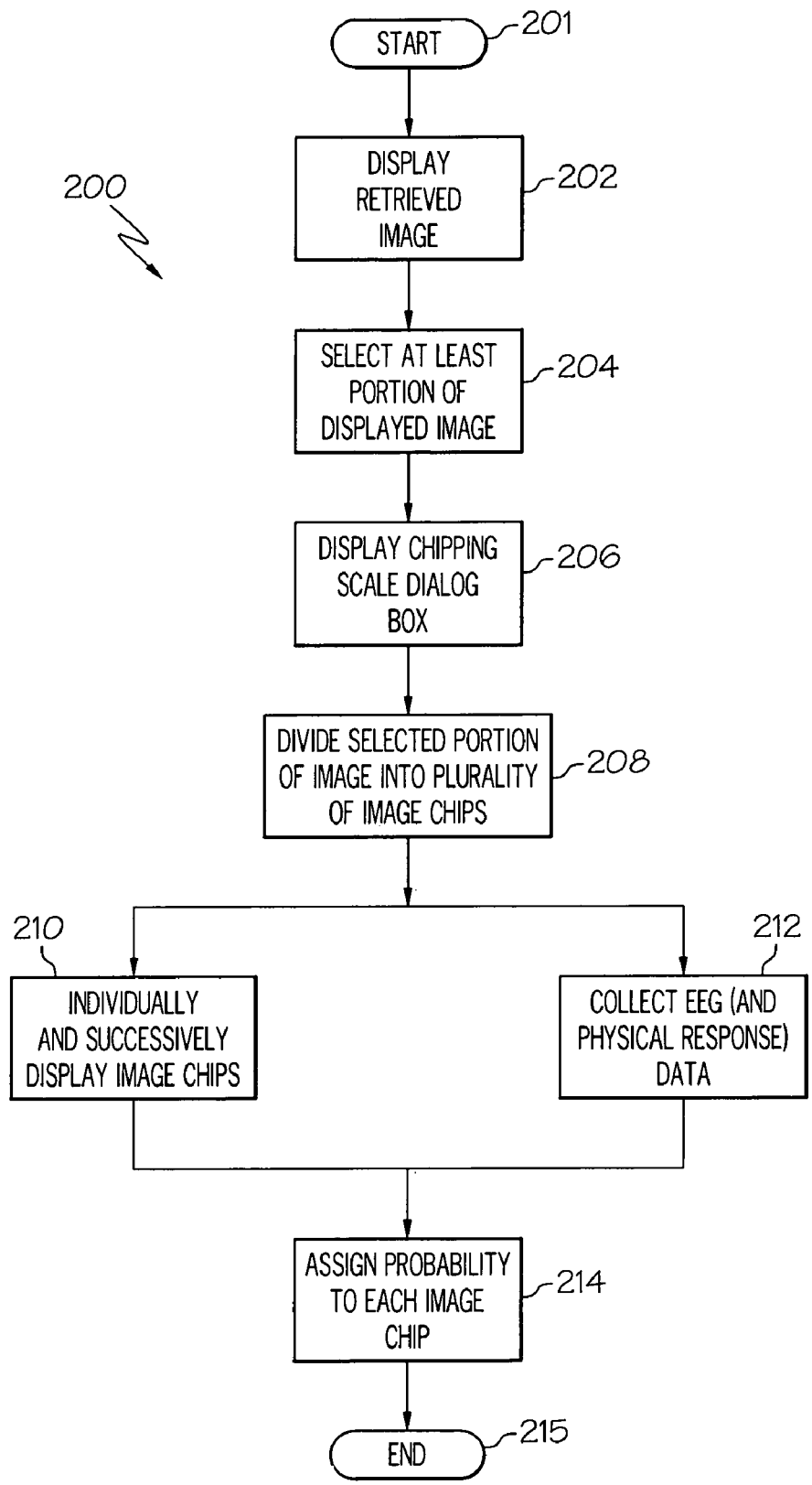
FIG. 2 depicts an exemplary process, in flowchart form, that may be implemented by the image triaging system of FIG. 1.

As was previously noted, the processor 106 receives neuophysiological data, physical response data, or both, and may additionally receive user state data. The processor 106, based at least in part on one or more of these data, assigns probabilities to discrete sections of an image. These assigned probabilities are representative of the likelihood that these discrete sections of the image include a target entity. The overall process 200 by which the processor 106 implements these outcomes is depicted in flowchart form in FIG. 2, and with reference thereto will now be described in more detail. Before doing so, however, it is noted that the depicted process 200 is merely exemplary of any one of numerous ways of depicting and implementing the overall process to be described. Moreover, before the process 200 is initiated, it is noted that, if neurophysiological data are collected, at least the neurophysiological data collector 104 has preferably been properly applied to the user 101, and appropriately configured to collect neurophysiological data. If included, the one or more user monitors 112 have also preferably been applied to the user 101, and appropriately configured to collect user state data. With this background in mind, it is additionally noted that the numerical parenthetical references in the following description refer to like steps in the flowchart depicted in FIG. 2.

Figure 3:
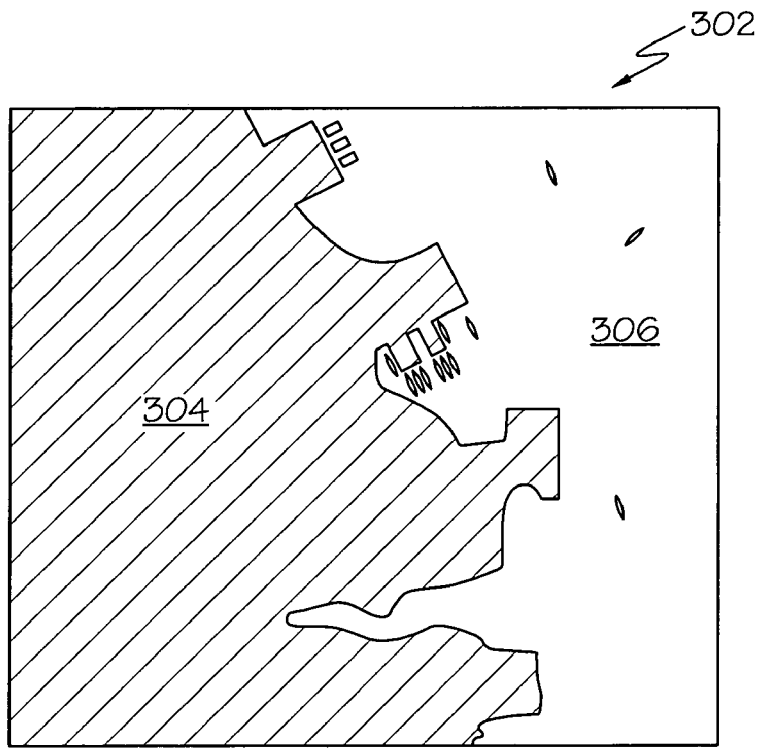
FIG. 3 depicts an exemplary broad area image that may be displayed using the system of FIG. 1.

Turning now to the description of the process 200, it is seen that when an image is retrieved from the image database 110, the processor 106 commands the display device 102 to display the image to the user 101 (202). In many instances, the retrieved and displayed image may be a broad area image. For example, the image may be a broad area satellite image that depicts a relatively large land area, a relatively large water (e.g., sea or ocean) area, or a relatively large area includes both land and water areas. An exemplary broad area image 302 that may be retrieved from the image database 110 and displayed on the display device 102 is depicted in FIG. 3. In the depicted example, the displayed broad area image 302 includes both land area 304 and water area 306.

Figure 4:
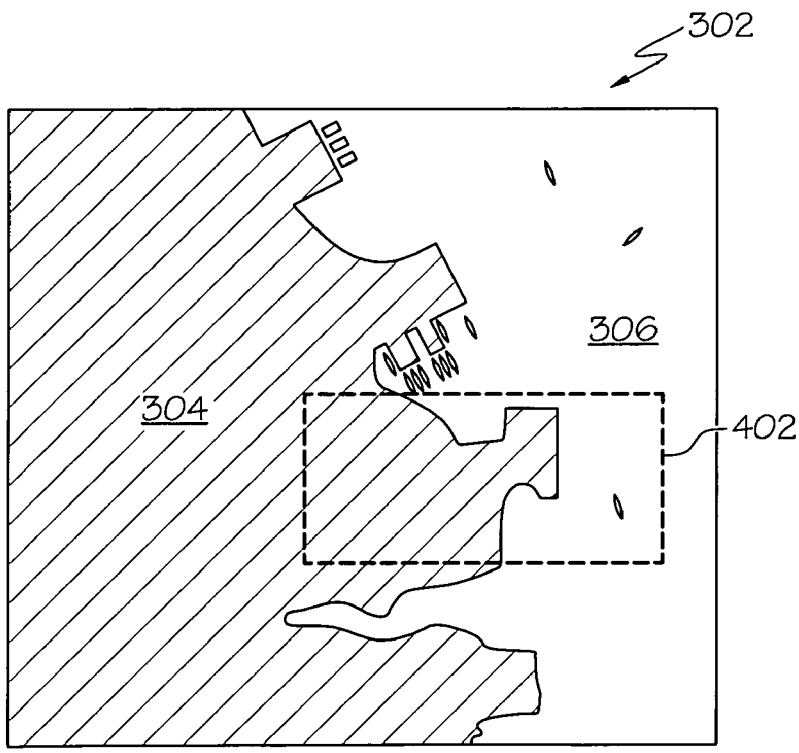
FIG. 4 depicts the exemplary broad area image and a selected portion of the broad area image of FIG. 3.

Rather than dividing the retrieved broad area image 302 into a plurality of image chips, and then displaying these image chips to the user, the system 100 is configured to allow the user 101 to select at least a portion of the displayed image 302 (204). In particular, as FIG. 4 depicts, the user 101 may select a particular region of interest 402 in the displayed image 302. It will be appreciated that the system 100 may be variously configured to implement this functionality, but in the depicted embodiment, the user 101 selects the region of interest 402 using the CCD 118. More specifically, the user 101 may position a non-illustrated cursor at one point on the displayed image 302 and while depressing, for example, one or more non-illustrated buttons on the CCD 118, move the cursor along the displayed image 302 to define the boundaries of the region of interest 402. No matter the specific manner in which the user 101 selects the region of interest 402, nor the specific user interface 108 that is used, the user interface 108 supplies appropriate user interface signals to the processor 106, and the processor 106, in response to these user interface signals, commands the display device 102 to display the boundaries of the region of interest 402.

Figure 5:
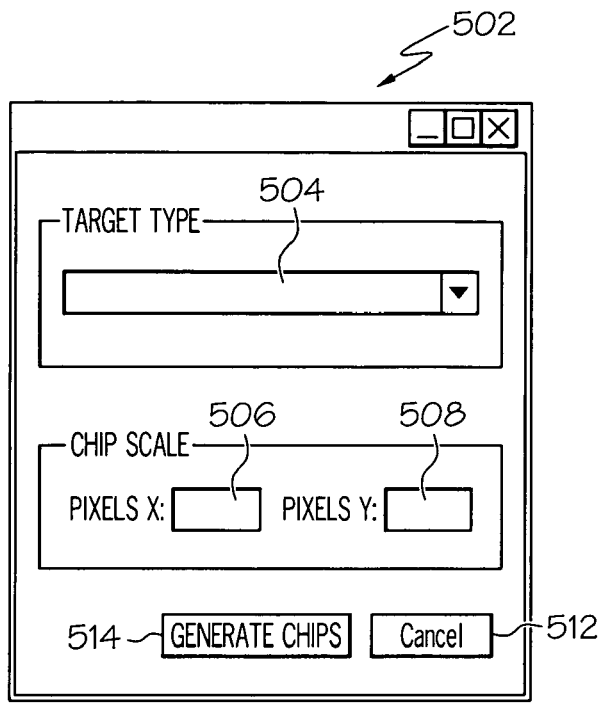
FIG. 5 depicts an exemplary dialog box that may be displayed by the system of FIG. 1.

After the user 101 defines the region of interest 402, the processor 106 commands the display device 102, either automatically or in response to other user input signals supplied from the user interface 108, to display a chipping scale dialog box (206). The chipping scale dialog box 502, an exemplary embodiment of which is depicted in FIG. 5, allows the user to specify a target entity to be searched for in the region of interest 402. Although this may be implemented using any one of numerous techniques, in the depicted embodiment the dialog box 502 includes a drop down target entity field 504 that, when selected using the user interface 108, displays a list of various predetermined target entity types from which a target entity type may be selected. It will be appreciated that in other embodiments, this field 504 may be blank, and the user may enter a target entity type via, for example, the user interface 108 (e.g., keyboard 122). It will additionally be appreciated that the specified target entity may vary. Some non-limiting examples include various types of land vehicles, seagoing vessels, special use land masses, weapons sites, or military bases, just to name a few examples.

As FIG. 5 further depicts, when a particular target entity type is selected (or entered) in the target entity field 504, the chipping scale dialog box 502 also displays, preferably automatically, a pair of image chip dimension fields 506, 508, and a pair of selectable buttons 512, 514. The image chip dimension fields 506, 508 define the dimensions (e.g., size) of each of the image chips into which the selected region of interest 402 will be divided. It will be appreciated that the image chip dimensions 506, 508 are preferably appropriate to the target type specified in the target entity field 504. The image chip dimensions displayed in the image chip dimension fields 506, 508 are preferably predetermined dimensions that are stored in memory within, or external to, the system 100. It will be appreciated, however, that the image chip dimension fields 506, 508 are preferably user modifiable. As such, the user 101, via the user interface 108, may modify the specific dimensions in either or both fields 506, 508. It will additionally be appreciated that in alternative embodiments, the image chip dimension fields 506, 508 may not automatically display predetermined dimensions. In such embodiments, it may be left to the user 101 to enter the desired dimensions in each field 506, 508.

Figure 6:
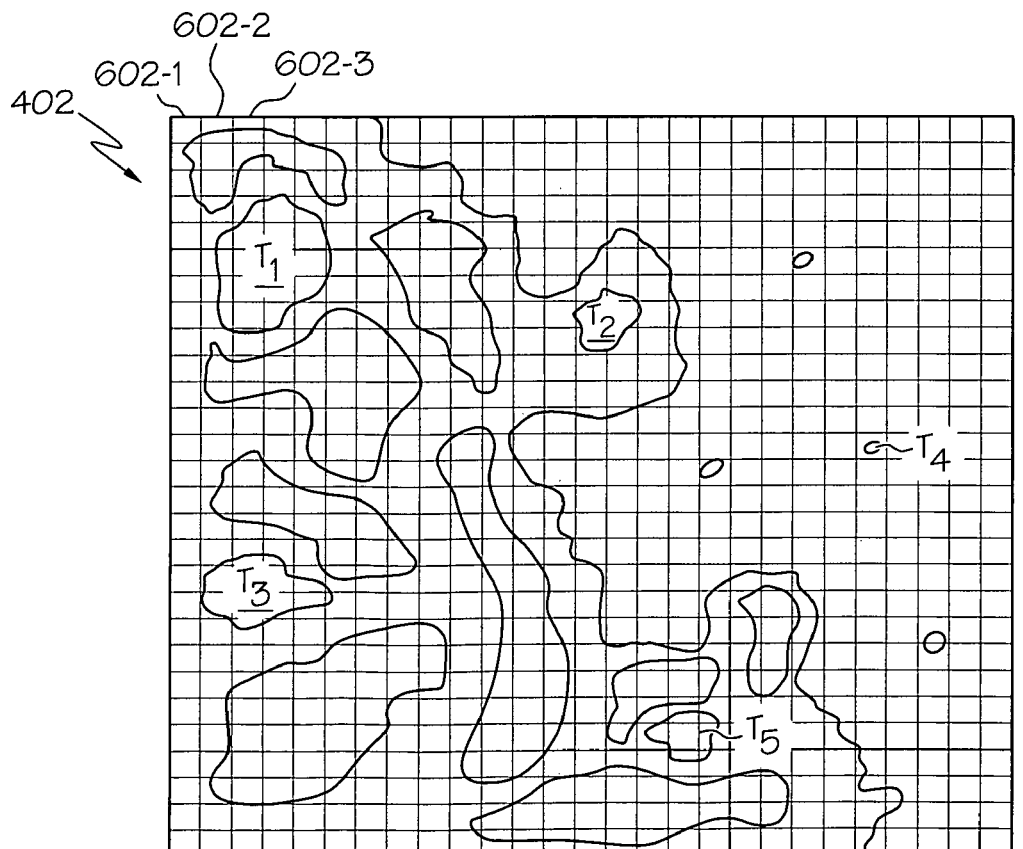
FIG. 6 depicts how the selected portion of the image depicted in FIG. 4 may be divided into individual image chips, in accordance with a particular embodiment of the present invention.

The user selectable buttons 512, 514, at least in the depicted embodiment, include a Cancel button 512 and a Generate Chips button 514. Each button 512, 514 may be selected by the user 101 via, for example, the user interface 108. If the user 101 selects the Cancel button 512, the processor 106 will cancel the operation and command the display device 102 to cease displaying the dialog box 502. Conversely, if the user 101 selects the Generate Chips button 514, the processor 106, and most notably the appropriate software being implemented by the processor 106, divides the selected region of interest 402 into a plurality of individual image chips (208), each having the image chip dimensions 506, 508 specified in the chipping scale dialog box 502. As was noted above, the image chip dimensions 506, 508 are based on the specified target entity in the target entity field 504. For example, and with reference now to FIG. 6, which is a simplified representation of a selected region of interest 402 in the broad area image 302, it is seen that the selected region of interest is divided into N-number of image chips 602 (e.g., 602-1, 602-2, 602-3, . . . 602-N). It will be appreciated that the number of image chips 602 that a selected region of interest is divided into may vary. As noted above, this will depend, at least in part, on the specified target entity and/or the dimensions specified in the image chip dimension fields 506, 508.

Returning once again to FIG. 2, after the selected region of interest 402 has been divided into the plurality of image chips 602, the image chips 602 are individually and successively displayed, on the display device 102, to the user 101 (210). In particular, the image chips 602 are preferably presented using a rapid serial visualization presentation (RSVP) technique. Thus, each image chip 602 is individually displayed, preferably at the same location on the display device 102, for a presentation time period, preferably in a predetermined sequence, and preferably at substantially equivalent luminance levels. The presentation time period of the image chips 602, which is referred to herein as the RSVP rate, may vary, and may be selected by the user 101.

While the image chips 602 are being displayed to the user 101, data such as, neurophysiological data, physical response data, or both, are collected from the user 101 (212). In some embodiments, as was previously noted, user state data may additionally be collected via the user interface 108 and the one or more state monitors 112. As was also previously noted, if neurophysiological data are collected, these data are preferably EEG data collected via the multi-channel EEG cap 114. It will be appreciated that, if collected, either the CCD 118 or the keyboard 122 may be used to collect the physical response data. In particular, the user 101 will hit either a predetermined button on the CCD 118 or a predetermined key on the keyboard 122 each time the user 101 believes a displayed image chip 602 includes a target entity, or at least a portion of a target entity. In the depicted embodiment, the selected region of interest 402 includes five target entities that, for simplicity of illustration, are labeled $T_1$ through $T_5$ on FIG. 6. It will be appreciated that in an actual physical implementation, the selected region of interest 402 may include any number of target entities.

During neurophysiological data collection, the processor 106, as previously noted, supplies image triggers, or brief pulses, to the neurophysiological data collector 104. The image triggers are supplied each time an image chip 302 is displayed. During subsequent processing, which is described further below, a segment of neuophysiological data and a segment physical response data are extracted around each image trigger. These segments, referred to as epochs, contain neuophysiological data and physical response data from a predetermined time before an image trigger to a predetermined time after the image trigger. It will be appreciated that the predetermined time period before and after each image trigger, and concomitantly the total length of each epoch of data, may vary.

After the neurophysiological data are collected and, in some embodiments, the physical response data and/or the user state data are collected, a probability is assigned to each image chip 602 (214). The probability that is assigned to each image chip 602 is based on these collected data, either alone or in combination, and is representative of the likelihood that the image chip 602 includes a target entity. It is noted that in a particular preferred embodiment, an epoch of neurophysiological data and an epoch of physical response data associated with each image chip 602 are supplied to one or more non-illustrated classifiers. The outputs of the classifiers are used to determine the probability to be assigned to each image chip 602.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of conducting image triage of an image that may include one or more target entities, comprising the steps of:
    specifying a target entity to be searched for in the image;
    dividing the image into a plurality of individual image chips, each image chip having a chip size based on the specified target entity;
    successively displaying each image chip for a presentation time period;
    collecting data from a user at least while each image chip is being displayed;
    for each image chip, assigning a probability that the image chip at least includes the specified target entity, based at least in part on the collected data;
    monitoring one or more states of the user, the one or more states of the user including one or more of user attention lapses, eye activity, and head movements; and
    supplying one or more alerts to the user based on the one or more states of the user.

2. The method of claim 1, further comprising:
    selecting at least a portion of the image to be searched.

3. The method of claim 2, wherein the step of specifying the target entity to be searched for in the image comprises specifying the target entity to be searched for in the selected portion of the image to be searched.

4. The method of claim 1, further comprising:
    automatically determining the chip size based on the specified target entity.

5. The method of claim 4, further comprising:
    displaying the automatically determined chip size to a user; and
    dividing the image into the plurality of individual image chips in response to an input from the user.

6. The method of claim 5, wherein the displayed chip size is user modifiable.

7. The method of claim 1, wherein the image chips are successively displayed in accordance with a rapid serial visualization (RSVP) paradigm.

8. The method of claim 1, further comprising:
    collecting the data from the user from a predetermined time period before an image chip is displayed to a predetermined time period after the image chip is displayed.

9. A system for conducting image triage of an image that may include one or more target entities, comprising:
    a display device operable to receive display commands and, in response thereto, to display an image;
    a user interface configured to receive input from a user and operable, in response to the input from the user, to at least supply user interface signals representative of a target entity to be searched for;
    a data collector in operable communication with the processor and configured to at least selectively collect data from the user;

one or more user state monitors configured to monitoring sensor one or more states of the user and supply user state data representative thereof, the one or more user states including one or more of user attention lapses, eye activity, and head movements; and a processor coupled to the display device, the data collector, and the user interface, the processor configured to receive the user state data, and:
  selectively retrieve an image,
  divide the image into a plurality of individual image chips each having a chip size based on the target entity to be searched for,
  successively command the display device to display each image chip for a presentation time period,
  assign a probability to each displayed image chip based at least in part on the collected data, each assigned probability representative of a likelihood that the image chip at least includes a target entity, and
  determine if the user is in a state that could adversely compromise probability assignment effectiveness, and selectively generate one or more alerts based on the one or more states of the user.

10. The system of claim 9, wherein the processor is further configured to command the display device to display the retrieved image.

11. The system of claim 10, wherein:
  the user interface is further configured, in response to the input from the user, to supply user interface signals representative of image portion selection commands; and
  the processor is responsive to the user interface signals representative of image portion selection commands to command the display device to display a boundary representative of a perimeter of a selected portion of the retrieved image.

12. The system of claim 11, wherein the processor is configured to divide the selected portion of the retrieved image into the plurality of image chips each having the chip size based on the target entity to be searched for.

13. The system of claim 9, wherein the processor is responsive to the user interface signals representative of the target entity to be searched for to automatically determine the chips size.

14. The system of claim 13, wherein:
  the processor is further configured to command the display device to display the automatically determined chip size and a user selectable button, the user selectable button selectable via the user interface; and
  the processor is responsive to selection of the user selectable via the user interface to divide the selected portion of the retrieved image into the plurality of image chips each having the chip size based on the target entity to be searched for.

15. The system of claim 9, wherein the processor is further configured to successively command the display device to display the image chips to the user in accordance with a rapid serial visualization (RSVP) paradigm.

16. The system of claim 9, wherein the data collector is configured to collect the data from the user from a predetermined time period before an image chip is displayed to a predetermined time period after the image chip is displayed.

17. A method of conducting image triage of an image that may include one or more target entities, comprising the steps of:
  selecting at least a portion of the image to be searched using a user interface;
  specifying a target entity to be searched for in the selected portion of the image;
  dividing the image into a plurality of individual image chips, each image chip having a chip size that is automatically determined based on the specified target entity;
  successively displaying each image chip for a presentation time period,
  monitoring one or more states of a user, the one or more states of the user including one or more of user attention lapses, eye activity, and head movements; and
  supplying one or more alerts to the user based on the one or more states of the user.

* * * * *